(12) United States Patent
Mackles

(10) Patent No.: US 7,332,528 B2
(45) Date of Patent: Feb. 19, 2008

(54) DRI NASAL SPRAYS

(76) Inventor: Leonard Mackles, 311 E. 23rd St., New York, NY (US) 10010

( * ) Notice: Subject to any disclaimer, the term of this patent is extended or adjusted under 35 U.S.C. 154(b) by 257 days.

(21) Appl. No.: 10/526,386

(22) PCT Filed: Sep. 10, 2003

(86) PCT No.: PCT/US03/28272

§ 371 (c)(1),
(2), (4) Date: Feb. 28, 2005

(87) PCT Pub. No.: WO2004/026362

PCT Pub. Date: Apr. 1, 2004

(65) Prior Publication Data

US 2006/0024237 A1    Feb. 2, 2006

(51) Int. Cl.
*A61K 47/00*    (2006.01)
(52) U.S. Cl. ............... 514/786; 514/957; 514/958
(58) Field of Classification Search ............... 514/957, 514/958, 786
See application file for complete search history.

(56) References Cited

U.S. PATENT DOCUMENTS 5,314,685 A * 5/1994 Tyle et al. ............... 424/401
5,897,858 A * 4/1999 Haslwanter et al. ..... 424/78.04
6,004,578 A * 12/1999 Lee et al. .................. 424/448

FOREIGN PATENT DOCUMENTS

DE    19925289 A1 * 12/2000
JP    07076526 A * 3/1995
WO    WO 9907341 A1 * 2/1999

OTHER PUBLICATIONS

Machine Translation of JP 07-076526.*
English Abstract of DE 199 25 289.*
English Translation of DE 199 25 289 A1 to Klocker et al, published Dec. 7, 2000.*
English Translation of JP 07-076526 to Omori et al, published Mar. 20, 1995.*

* cited by examiner

*Primary Examiner*—Sreeni Padmanabhan
*Assistant Examiner*—Renee Claytor
(74) *Attorney, Agent, or Firm*—Omri M. Behr

(57) ABSTRACT

There are provided safe, tasteless, odorless, non-aqueous liquid spray compositions formulated for administration to the nasal cavity consisting essentially of pharmacologically acceptable non aqueous liquid carrier in which said bioactive material is directly insoluble, a pharmacologically acceptable water insoluble ester of a water soluble acid soluble in said carrier, a pharmacologically acceptable water soluble glycol soluble in said ester and a pharmacologically acceptable water soluble bio-active material soluble in said glycol but not directly soluble in the carrier. There are also provided methods of producing and administering such compositions.

19 Claims, No Drawings

DRI NASAL SPRAYS

RELATED APPLICATIONS

This application claims priority of applicants U.S. application Ser. No. 10/253,073 filed Sep. 23, 2002 and Ser. No. 10/406,869 filed Apr. 4, 2003.

BACKGROUND OF THE INVENTION

1. Field of the Invention

Safe, tasteless, odorless, non irritating, non aqueous spray compositions containing bioactive material administrable via the nasal cavity.

2. Discussion of the Prior Art

The use of nasal sprays to provide relief from the nasal stuffiness of colds and allergic rhinitis is widespread. Various sympathomimetic amines have been used to provide relief. Nasal decongestants stimulate the alpha-adrenergic receptors of the vascular smooth muscle. This constriction results in shrinkage of the engorged mucous membranes which promotes drainage; improves nasal ventilation and relieves the feeling of stuffiness.

Many decongestants are commercially available and are used to give various lengths of relief from 4 hours up to 12 hours. All of these decongestants are water soluble and are delivered in aqueous spray systems.

The decongestant solutions are delivered by spray from either a flexible plastic container that produces a mist when squeezed or by a hand operated mechanical pump.

These aqueous sprays are wet, cold and drip from the nose. They are very uncomfortable to use. Since they are aqueous based and the nozzle is inserted in the nostril, bacterial contamination of the product easily occurs. Nasal sprays are difficult to preserve.

The mucous layer lining the epithelium represents a barrier to drug absorption along with mucociliary clearance mechanisms of the nose leads to short residence time of aqueous systems at the site of absorption which limits the systemic availability of the drug.

SUMMARY OF THE INVENTION

The invention is directed to compositions of incorporating an effective dosage of decongestant or other drug from a safe, non-aqueous, non-irritating, tasteless and odorless liquid carrier system that delivers an extremely fine, non-dripping, warm, pleasant spray to the nasal cavity from either a squeeze bottle or pump spray system.

There is provided a non-aqueous liquid spray composition for a bioactive material containing, in fact consisting essentially of, a pharmacologically acceptable non aqueous liquid carrier in which said bioactive material is directly insoluble, a pharmacologically acceptable water insoluble ester of a water soluble acid soluble in said carrier,a pharmacologically acceptable water soluble glycol soluble in said ester, a pharmacologically acceptable water soluble bio-active material soluble in said glycol but directly insoluble, that is to say cannot be directly dissolved in said carrier. As used herein, the term "consisting essentially of" means that the foregoing components and their order of mixing are central to the invention. The compositions may contain other additives such as odorants, colorants, flavorants and the like which do not interfere, by enhancement or otherwise, with the mechanism of formation thereof or the desirable properties thereof as set forth herein.

The spray compositions of the present invention are produced by the sequential steps of dissolving the bio-active material in a glycol, dissolving the resultant solution in a water insoluble ester of a water soluble acid and dissolving said further resultant solution in a suitable carrier as discussed above.

The spray compositions of the present invention containing the appropriate bio-active material may be administered to a subject in need of same by spraying a pharmacologically effective amount of such a composition into the nasal cavity of said subject. This may be done using any spray method, such as using a pump spray device or a squeeze bottle spray, the latter being inexpensive and especially suitable.

The system of the present invention possesses several advantages over the aqueous nasal administration systems heretofore available. It provides a fine, warm, dripless, non-irritating spray, which, depending on the drug used, gives 4-12 hour decongestant relief. Because the system is non-aqueous, no preservatives are needed and the system will resist recontamination.

Furthermore because the system is anhydrous, it will wet out and cling to the mucous membrane of the nasal passages. Being water resistant, it will resist removal by the mucociliary clearance mechanism; thereby allowing more contact time at the site. The drugs will partition from the system and be adsorbed by the mucosa giving faster onset of action and greater symptom relief.

The system works exceptionally well with all commercially available spray systems. In fact, the efficacy of squeeze bottle system is comparable to the more expensive pump spray delivery.

All ingredients are safe for use in the nose. The esters and glycols used manifest a moisturizing effect which will keep the nasal tissues soft and supple thereby eliminating nasal dryness. In addition to the bio-active materials to be administered, the spray compositions may also include conventional additives such as essential oils, fragrances, flavors, sweeteners, menthol, peppermint oil, pine tar, camphor, benzoin preparations, tolu, fumed silicon dioxide and the like.

DESCRIPTION OF THE PREFERRED EMBODIMENTS

Suitably the carrier is a cyclopentasiloxane, preferably decamethylcyclopentylsiloxane, a triglyceride, a diglyceride, and mixtures of said glycerides. It especially desirable that the carrier is decamethylcyclopentylsiloxane, a medium chain diglyceride, a medium chain triglyceride and mixtures of said glycerides, most suitably wherein these moieties are selected from the group consisting of caprylic and capric acids. As used herein the term "medium chain" means a chain wherein the alkyl moiety has between 8 and 12 carbon atoms and mixtures of such chains. Suitably the alkylene moiety of said glycerides contain 3-6 preferably 3 carbon atoms.

Suitably the ester is a lactate ester, desirably it is a $C_{12}$-$C_{18}$ alkyl lactate, preferably where the alkyl group is cetyl, lauryl, isostearyl and myristyl and mixtures thereof.

Preferably, the glycol is a $C_3$ to $C_8$ glycol, including but not limited to propylene, dipropylene, hexylene, 1,3-butylene, diethylene, triethylene, tetrapropylene and tetraethylene glycols, polyethylene glycol 200 and polypropylene glycol 425 and 2-methyl-1,3-propane diol and mixtures thereof While the invention is not limited thereto, bio-active materials suitable for use in this invention include those selected from the group consisting of decongestants, antihistamines, analgesics such as butorphanol tartrateantitussives, anticholinergics, steroids, suitably corticosteroids such as triamcinolone acetonide, antibiotics, antispasmotics, such as beclamethasone dipropionate, brochodilators, such as ipratropium bromide, fluticasone pripionate, albuterol sulfate, vitamins, such as vitamine B-12 or cyanocobalamine, hormones, suitably peptide hormones such as calcitonin-salmon, antihypertensives such as propranolol, and antimicrobials.

Especially suitable for purposes of this invention as the bio-active material are decongestants. Most suitably oxymetazoline, xylometazoline, naphazoline, phenylephrine, ephedrine in water soluble form especially when in the form of a pharmacologically acceptable salt, such as a hydrochloride or sulfate.

The ranges of the components of the spray composition are suitably from about 50-about 90 wt. % of the carrier, from about 10-about 40 wt % of the water soluble ester, from about 1 to about 5 wt. % of the water soluble glycol, and from about 0.01 to about 2 wt. % of the bio-active material, to a total wt % of 100. Preferably the ranges are from about 60 about 90 wt. % of the carrier, from about 10 about 30 wt % of the water soluble ester, from about 1 to about 3 wt. % of the water soluble glycol and from about 0.01 to about 2 wt. % of the bio-active material.

The sprays of the present invention are administered by spraying into the nasal cavity. The actual volume sprayed may lie between about 20 and about 80 micro liters. This amount is readily set by those skilled in the art of valve design for squeeze bottles and spray bottles. Thus the dosage of bio-active delivered is determined by its concentration in the composition. The needed frequency of administration may be readily determined by those skilled in the art based on present knowledge and not requiring undue experimentation.

EXAMPLES (All quantities are in wt. % unless otherwise noted)

Example #1 Nasal Decongestant 12 Hour Duration

| | |
|---|---|
| 1. Oxymetazoline.HCl | 0.05 |
| 2. Propylene Glycol | 2.50 |
| 3. $C_{12}$-$C_{15}$ Alkyl Lactate | 20.00 |
| 4. Dimethylcyclopentasiloxane | 77.45 |
| | 100.00 |

Components #1 and #2 are heated to 50° C. until clear and uniform then the batch is cooled the #3 is added with mixing and when clear, #4 is added and mixed. The batch may then be charged to a spray container in suitable quantities.

Example #2 Nasal Decongestant 8 Hour Duration

| | |
|---|---|
| 1. Xylometazoline.HCl | 0.10 |
| 2. Propylene Glycol | 2.50 |
| 3. $C_{12}$-$C_{15}$ Alkyl Lactate | 20.00 |
| 4. Cyclopentasiloxane | 77.40 |
| | 100.00 |

This mixture is prepared in accordance with the procedures of Example #1

Example #3 Nasal Decongestant 4 Hour Duration

| | |
|---|---|
| 1. Phenylephrine.HCl | 0.50 |
| 2. Propylene Glycol | 5.00 |
| 3. $C_{12}$-$C_{15}$ Alkyl Lactate | 30.00 |
| 4. Cyclopentasiloxane | 64.50 |
| | 100.00 |

This mixture is prepared in accordance with the procedures of Example #1

Example #4 Nasal Decongestant 12 Hour Duration

| | |
|---|---|
| 1. Oxymetazoline.HCl | 0.05 |
| 2. 1,3-Butylene Glycol | 2.50 |
| 3. Lauryl Lactate | 20.00 |
| 4. Cyclopentasiloxane | 77.45 |
| | 100.00 |

This mixture is prepared in accordance with the procedures of Example #1

Example #5 Nasal Decongestant and Antihistamine

| | |
|---|---|
| 1. Oxymetazoline.HCl | 0.05 |
| 2. Chlorpheniramine Maleate | 0.20 |
| 3. Propylene Glycol | 2.50 |
| 4. Myristyl Lactate | 20.00 |
| 5. Cyclopentasiloxane | 77.25 |
| | 100.00 |

Components #1, #2 and #3 are heated to 50° C. until clear and uniform then the batch is cooled the #4 is added with mixing and when clear, #5 is added and mixed. The batch may then be charged to a spray container in suitable quantities.

Example #6 Nasal Decongestant

| | |
|---|---|
| 1. Oxymetazoline.HCl | 0.05 |
| 2. Propylene Glycol | 2.00 |
| 3. Isostearyl Lactate | 23.00 |
| 4. Cyclopentasiloxane | 74.95 |
| | 100.00 |

This mixture is prepared in accordance with the procedures of Example #1

Example #7 Nasal Decongestant 12 Hour Duration

| | |
|---|---|
| 1. Oxymetazoline.HCl | 0.05 |
| 2. Propylene Glycol | 1.50 |
| 3. $C_{12}$-$C_{15}$ Alkyl Lactate | 20.00 |
| 4. Caprylic/Capric Triglyceride | 78.45 |
| | 100.00 |

This mixture is prepared in accordance with the procedures of Example #1

Example #8 12 Hour Duration Nasal Decongestant

| | |
|---|---|
| 1. Oxymetazoline.HCl | 0.05 |
| 2. Propylene Glycol | 1.5 |
| 3. $C_{12}$-$C_{15}$ Alkyl Lactate | 10.00 |
| 4. Propylene Glycol Dicaprylate/Dicaprate | 84.45 |
| | 100.00 |

This mixture is prepared in accordance with the procedures of Example #1

The invention claimed is:

1. A method of producing a liquid spray composition for administration of a bioactive material to the nasal cavity consisting essentially of:
   a) a pharmacologically acceptable non aqueous liquid carrier selected from the group consisting of diglycerides, triglycerides and mixtures thereof in which said bioactive material is directly insoluble,
   b) a pharmacologically acceptable water insoluble ester of a water soluble acid soluble in said carrier,
   c) a pharmacologically acceptable water soluble glycol soluble in said ester, comprising from about 1 to about 5 wt. % of the total composition,
   d) a pharmacologically acceptable water soluble bio-active material soluble in said glycol but directly insoluble in said carrier said spray being non-aqueous tasteless, odorless,
   which consists essentially of the sequential steps of dissolving the bio-active material of (d) in a glycol of (c), dissolving said solution of (d) in (c) in an ester of (b) and dissolving said solution of {(d) in (c) in (b)}in a carrier of (a).

2. The method of claim 1 wherein the carrier is selected from the group consisting of a medium chain diglyceride, a medium chain triglyceride and mixtures of said glycerides.

3. The method of claim 2 wherein the carrier is selected from the group consisting of a medium chain ethylene diglyceride, medium chain propylene diglyceride, a medium chain propylene triglyceride and mixtures of said glycerides.

4. The method of claim 3 wherein the glyceride moieties are selected from the group consisting of caprylic and capric glycerides.

5. The composition produced by the method of claim 1 consisting essentially of
   a) from about 50-about 90 wt. % of the carrier,
   b) from about 10-about 40 wt. % of the water insoluble ester,
   c) from about 1-about 5 wt. % of the water soluble glycol,
   d) from about 0.01 -about 2 wt. % of the bio-active material.

6. The composition of claim 5 consisting essentially of
   a) from about 60 about 90 wt. % of the carrier,
   b) from about 10 about 20 wt. % of the water insoluble ester,
   c) from about 1 to about 3 wt. % of the water soluble glycol,
   d) from about 0.01 to about 2 wt. % of the bio-active material.

7. The composition of claim 6 wherein the glycol is a $C_3$ to $C_8$ glycol.

8. The composition of claim 7 wherein the glycol is selected from the group consisting of polyethylene glycol and propylene glycol.

9. The composition of claim 5 wherein the ester is a lactate ester.

10. The composition of claim 9 wherein the lactate ester is a $C_{12}$ - $C_{15}$ alkyl lactate.

11. The composition of claim 10 wherein the alkyl group is selected from the group consisting of cetyl, lauryl, isostearyl and myristyl and mixtures thereof.

12. The composition of claim 5 wherein the bio-active material is selected from the group consisting of decongestants, antihistamines, antitussives, anticholinergics, steroids, antibiotics, analgesics, antispasmotics, brochodilators, vitamins, hormones, antihypertensives and antimicrobials.

13. The composition of claim 5 wherein the bio-active material is a decongestant.

14. The composition of claim 13 wherein the bio-active material is selected from the group consisting of oxymetazoline, xylometazoline, naphazoline, phenylephrine, ephedrine in water soluble form.

15. The composition of claim 14 wherein the bio-active material is in the form of a pharmacologically acceptable salt.

16. A method of administering a bio-active material to a subject in need of same which consists essentially of spraying a pharmacologically effective amount of a composition of claim 5 into the nasal cavity of said subject.

17. The method of claim 16, wherein the bio-active material is selected from the group consisting of decongestants, antihistamines, antitussives, anticholinergics, steroids, analgesics, antibiotics, antispasmotics, brochodilators, vitamins, hormones, antihypertensives and antimicrobials.

18. The method of claim 17, wherein the bio-active material is a decongestant.

19. The method of claim 18, wherein the bio-active material is selected from the group consisting of oxymetazoline, xylometazoline, naphazoline, phenylephrine, ephedrine in water soluble form.

* * * * *